(12) United States Patent
Tyrrell et al.

(10) Patent No.: US 9,081,006 B2
(45) Date of Patent: Jul. 14, 2015

(54) RAPID HOMOGENEOUS IMMUNOASSAY USING ELECTROPHORESIS

(75) Inventors: Steven Patrick Tyrrell, Erie, CO (US); Barry Vant-Hull, Boulder, CO (US)

(73) Assignee: LYZER DIAGNOSTICS, INC., Boulder, CO (US)

( * ) Notice: Subject to any disclaimer, the term of this patent is extended or adjusted under 35 U.S.C. 154(b) by 1253 days.

(21) Appl. No.: 12/023,450

(22) Filed: Jan. 31, 2008

(65) Prior Publication Data
US 2008/0230388 A1    Sep. 25, 2008

Related U.S. Application Data

(60) Provisional application No. 60/899,831, filed on Feb. 7, 2007.

(51) Int. Cl.
*G01N 27/447* (2006.01)
*G01N 33/561* (2006.01)
*B01D 57/02* (2006.01)

(52) U.S. Cl.
CPC .............. *G01N 33/561* (2013.01); *B01D 57/02* (2013.01); *G01N 27/447* (2013.01)

(58) Field of Classification Search
CPC .................................................. G01N 33/561
USPC .............. 435/7.5, 6, 34, 287.1, 7.4, 4, 7.1; 436/531, 532, 516, 512, 518, 530; 204/616, 617, 618, 451, 601; 205/467, 205/466
See application file for complete search history.

(56) References Cited

U.S. PATENT DOCUMENTS 4,560,649 A    12/1985    Saxena
4,628,035 A    12/1986    Tokinaga
(Continued)

FOREIGN PATENT DOCUMENTS

WO    WO2000/060120    10/2000
WO    WO2007/041692    4/2007

OTHER PUBLICATIONS

International Search Report for International application No. PCT/US08-52610, mailed Jul. 7, 2008.
(Continued)

*Primary Examiner* — Luan Van
*Assistant Examiner* — Gurpreet Kaur
(74) *Attorney, Agent, or Firm* — Peter B. Scull; Hamilton DeSanctis & Cha LLP

(57) ABSTRACT

The present invention concerns methods, compositions and apparatus for detection and/or determination of concentration of target molecules. In preferred embodiments the methods comprise allowing target molecules to form a complex with a first binding agent conjugated to a detection molecule and a second binding agent conjugated to a capture molecule, allowing the complex to further bind to an essentially uncharged polymer capable of binding to the capture agent, and performing a vertical gradient electrophoresis to separate the complex from unbound target, first and second binding agents and polymer. The intact complex is concentrated by electrophoresis at a stacking layer and the detection molecule is detected and/or quantified. Because the complex contains a very high mass to charge ratio, it becomes essentially immobile at the stacking layer, while unbound components migrate through the stacking layer and are separated from the complex. This provides a very rapid and sensitive assay that can detect very low concentrations of target molecules in short time.

10 Claims, 12 Drawing Sheets

Neutravidin     Target protein     Biotin-polymer

Biotin-Ab     FITC Ab     Linear acrylamide

(56) References Cited

U.S. PATENT DOCUMENTS

| | | | |
|---|---|---|---|
| 4,687,732 A * | 8/1987 | Ward et al. | 435/6.12 |
| 5,047,324 A | 9/1991 | Fredrickson | |
| 5,571,680 A | 11/1996 | Chen | |
| 5,626,735 A * | 5/1997 | Chu | 204/606 |
| 6,214,187 B1 | 4/2001 | Hammond et al. | |
| 6,428,668 B1 | 8/2002 | Ansorge | |
| 2001/0023825 A1* | 9/2001 | Frumin et al. | 204/458 |
| 2002/0197614 A1 | 12/2002 | Weir | |
| 2004/0195103 A1 | 10/2004 | Zhou | |
| 2005/0170362 A1 | 8/2005 | Wada | |
| 2006/0172340 A1* | 8/2006 | Wohlstadter et al. | 435/7.1 |
| 2006/0211055 A1* | 9/2006 | Hafeman et al. | 435/7.5 |

OTHER PUBLICATIONS

Lee Bao-Shiang, et al., "Catching protein antigens by antibody affinity electrophoresis," Electrophoresis, vol. 25, No. 20:3331-3335, Oct. 20, 2004.

Lee Bao-Shiang, et al., "Mass spectrometric detection of biotinylated peptides captured by avidin functional affinity electrophoresis," Rapid Communications in Mass Spectrometry, Viol:19, No. 7:888-892, Feb. 23, 2005.

Supplementary European Search Report for European Application No. EP 08 72 8677, Dated Mar. 17, 2010.

* cited by examiner

Fig 1

$a$ = centrifugal acceleration [cm/s$^2$]

$e$ = unit charge of electrons or protons [1.6 x 10$^{-19}$ C (coulombs)]

$f$ = applied force [g cm/s$^2$]

$f_f$ = frictional force [g cm/s$^2$]

$r$ = hydrodynamic radius of the molecule [cm]

$m$ = mobility [s/g]

$M$ = molecular weight [g/mole]

$N$ = Avogadro's Number (6.023 x 10$^{23}$ /mole)

$s$ = Svedberg Coefficient [10$^{-13}$ s]

$u$ = electrophoretic mobility [cm$^2$/s-V]

$v$ = velocity of the particle through the fluid [cm/s]

$z$ = net charge on the molecule $\eta$ = viscosity of fluid [g/cm-s]

$\rho$ = density of the molecule [g/cm$^3$]

$\rho_f$ = density of the fluid [g/cm$^3$]

$\psi$ = electrical field [volt/cm]

Fig 2

$$f_f = 6\pi r \eta v \qquad \text{(Eq 1)}$$

Fig 3A

$$m = v/f_f = 1/(6\pi r \eta) \qquad \text{(Eq 2a)}$$

Fig 3B

$$r = \sqrt[3]{\frac{3V}{4\pi}} = \sqrt[3]{\frac{3M}{4\pi N \rho}} \qquad \text{(Eq 2b)}$$

Fig 3C

$$m = \sqrt[3]{\frac{N \rho}{162 \pi^2 \eta^3 M}} \qquad \text{(Eq 2c)}$$

Fig 4

$$v = fm \qquad (Eq\ 3)$$

Fig 5

$$v = zem\psi \quad . = u\psi \qquad (Eq\ 4)$$

Fig 6

$$u = ezm \times 10^7 \qquad (Eq\ 5)$$

Fig 7A $$s = v/a \cdot 10^{13} = \frac{(\rho - \rho_f)}{\rho_f} \frac{M}{N} am/a \cdot 10^{13} \qquad \text{(Eq 6a)}$$

Fig 7B $$m = \frac{\rho N s}{(\rho - \rho_f) M} \times 10^{-13} \qquad \text{(Eq 6b)}$$

Fig 8A

$$m = \sqrt[3]{\frac{(6 \times 10^{23})(1.2)}{162\pi^2 (0.01)^3 (1.5 \times 10^5)}} = 2.1 \times 10^7 \, s/g \qquad \text{(Eq 7a)}$$

Fig 8B

$$m = \frac{(1.2)(6 \times 10^{23})(7 \times 10^{-13})}{(1.2-1.0)(1.5 \times 10^5)} = 1.7 \times 10^7 \, s/g \qquad \text{(Eq 7b)}$$

| [IL-6], pM | Peak Area | Peak Area (Bkg subtr.) | Exposure Time, msec |
|---|---|---|---|
| 0 | 24068 | 0 | 7000 |
| 1 | 21785 | -2283 | 7000 |
| 3.17 | 29971 | 5903 | 7000 |
| 10 | 37966 | 13898 | 7000 |
| 31.7 | 53356 | 29288 | 7000 |
| 100.1 | 126509 | 102441 | 7000 |
| 316.5 | 419017 | 394949 | 7000 |
| 1000 | 1543735 | 1519667 | 7000 |

1 nM anti-IL6 biotin pAb
1 nM anti-IL6 fluorescein-mAb

RAPID HOMOGENEOUS IMMUNOASSAY USING ELECTROPHORESIS

RELATED APPLICATIONS

The present application claims the benefit under 35 U.S.C. §119(e) of U.S. Provisional Patent Application Ser. No. 60/899,831, filed Feb. 7, 2007, the entire text of which is incorporated herein by reference.

FIELD OF THE INVENTION

The present invention relates to methods, compositions and/or apparatus for the detection of the presence and/or determination of the concentration of proteins or other target molecules in a sample. The methods, compositions and/or apparatus are effective for detection and/or concentration measurement over a wide range of concentrations of the target molecule(s). More particularly, the methods may be performed in a shorter time (a few minutes) and at greater sensitivity than is possible with current alternative methods.

BACKGROUND

The detection of proteins at low concentrations is of paramount importance in the areas of medicine, food testing, biological research, and the detection of biowarfare agents. By far, the most common tools for measuring proteins are antibodies, which are proteins produced by the immune systems of higher animals. Tests which use antibodies (or similar binding agents) are commonly known as "immunoassays" (Gosling, 1990).

A common alternative to using the entire antibody molecule is to use just the binding regions of the antibody. A variety of antigen-binding antibody fragments are known, such as Fab fragments (Gosling, 1990), Fab' fragments, $F(ab)_2$ fragments, $F(ab')_2$ fragments, scFv fragments, etc. Fab fragments may be obtained either by cleaving a whole antibody molecule biochemically, or by synthesizing them in cell cultures using genetic engineering techniques.

Another recently developed alternative to antibodies are aptamers (Gold et al., 1995; Drolet et al., 1996). Aptamers are nucleic acids (RNA or DNA or their derivatives) which have been designed to share many of the binding characteristics of antibodies. Aptamers offer the advantages of being produced in vitro in a comparatively short time, of having a long shelf-life, being easy to modify chemically, and of potentially exhibiting better binding characteristics than antibodies. Disadvantages include high cost, and low stability in some biological fluids.

Immunoassays are often characterized as being either "heterogeneous" or "homogeneous". There is some confusion in the field as to what these terms mean. In some cases, the term "heterogeneous" is taken to imply that the bound complexes are separated (by any means) from the unbound molecules before detection, while the term "homogeneous" implies that no separation takes place. Another common meaning for the term "heterogeneous" (that is used in this disclosure) implies that the assay makes use of both a solid and a solution phase, in which attachment of the complex to the solid phase allows the unbound molecules to be washed away (or vice versa) before detection, while the term "homogeneous" implies that the binding, separation (if any), and detection steps occur in the solution phase. In most cases, the differing definitions make little difference in how an assay is classified, as most separation or washing steps involve binding to a solid support, and thus assays involving separation or washing would be classified as heterogeneous by either definition. The major exception is separation by electrophoresis, which would cause an assay to be classified as heterogeneous according to the first set of definitions, and homogeneous according to the second set of definitions. This disclosure uses the second set of definitions.

Therefore, in this disclosure, a heterogeneous assay involves binding the antibody-target protein complex to a surface during the test procedure and then washing away any remaining unbound sample and antibody prior to measuring the amount of protein in the sample. A homogeneous assay, on the other hand, permits the sample and antibodies to be mixed together and the result determined without any binding to a surface or washing. Each approach has both well-defined benefits and limitations (Ronkainen-Matsuno, et al. 2002).

Heterogeneous assays can have excellent sensitivity and specificity and can be performed in formats that provide for very high-throughput testing systems. These formats can also be adapted to test for virtually any antigen. Limitations include slow testing times requiring relatively sophisticated instrumentation to perform in large numbers, and the added costs associated with the surface-binding and washing steps.

Homogeneous assays can be very fast, are easily adaptable to new proteins and platforms, and can be very cost effective. Limitations include potentially lower specificity and sensitivity. In addition, these formats are typically restricted to small target antigens.

Electrophoresis is a technique that, in certain cases, may be used in place of the washing of complexes that are bound to a solid support, thereby converting what is normally a heterogeneous protein assay into a homogeneous assay. Electrophoresis is commonly used to separate molecules (usually large ones such as proteins or nucleic acids) based on their size and electrical charge (Oda and Landers, 1997). Positive and negative electrodes are placed in a solution containing the molecules to be separated, and a voltage drop is applied between the electrodes. In general, positively charged molecules will migrate toward the negatively charged electrode, while negatively charged molecules will migrate toward the positively charged electrode. The speed at which the molecules migrate is directly proportional to their charge, and inversely proportional to their size. Small, highly charged molecules move faster than large, lesser charged molecules. However, densely packed molecules move faster than loosely conformed molecules, so that two molecules of the same mass and charge may migrate at different rates. Higher voltage drops cause faster migration, while higher concentrations of other charged molecules in the solution cause slower migration.

There are many variations of electrophoresis. The solution through which the molecules move may be free, usually in capillary tubes, or it may be embedded in a matrix. Common matrices include polyacrylamide gels, agarose gels, and filter paper. The matrix serves to sieve the molecules according to size, leading to better separations. The pH (acidity) of the solution affects the charge of the molecules, and may be varied (even from one end of the matrix to the other) to affect the migration rate of the molecules. The solution may include denaturing agents such as urea, which cause protein and nucleic acid molecules to unfold, so that migration rates for molecules of the same mass and charge will be identical. The sample to be electrophoresed may be prepared with a detergent such as SDS, which coats all proteins to nullify charge differences, so that migration rates depend on mass, but not on charge. However, for most assays requiring binding agents such as antibodies or aptamers, both the protein and the binding agents need to be kept close to their natural state, so that processes that change the pH or denature the proteins are not viable options.

Present methods for detecting and/or determining the concentration of molecules in solution fail to combine short assay time, high sensitivity and ability to assay larger sample volumes required to detect and/or quantify target molecules present at very low concentration. A need exists in the field for improved analytical techniques for detection and/or concentration determination of molecules.

SUMMARY OF THE INVENTION

In various embodiments, the present invention generally relates to the detection and/or determination of the concentration of proteins or other target molecules using specific binding agents such as antibodies, aptamers, or designed small-molecule binders. Preferred embodiments relate to the detection of target molecules by (1) binding the target molecule to two binding agents, one conjugated to a detection molecule, and the other conjugated to capture molecule (for instance, biotin) to form a target complex; (2) utilizing electrophoresis to move complexed and non-complexed molecules through a region containing polymers bound to the cognate of the capture molecule (for instance, streptavidin), by which the mobility of the target complex is dramatically reduced; (3) continuing electrophoresis so that the non-complexed molecules are separated from the complexed molecules which are bound to the polymer; and (4) determination of the target complex concentration by quantitation of the detection molecule.

In certain embodiments, the disclosed methods convert a sandwich immunoassay from a heterogeneous assay to a homogeneous assay, thereby eliminating many of the labor-intensive and costly steps normally associated with heterogeneous assays such as the sandwich ELISA assay. In other embodiments, the disclosed methods gain the kinetic advantages associated with performing an assay completely in the solution phase. The present invention will allow a sandwich immunoassay to be performed in minutes instead of hours and at a reduced cost.

BRIEF DESCRIPTION OF THE DRAWINGS

FIG. 1—A list of the symbols used in the equations. In most cases, the quantities are in units of centimeter-gram-second (c-g-s units).

FIG. 2—Equation 1 relates the frictional force experienced by a particle moving through a fluid to its velocity, radius, and viscosity of the fluid.

FIG. 3A—Equation 2a defines the mobility as the velocity of a particle divided by the frictional force it experiences, and thence to its radius and the viscosity of the fluid it moves through.

FIG. 3B—Equation 2b relates the radius of a sphere to its volume, and thence to its density and mass.

FIG. 3C—Equation 2c then relates the mobility to a particle's mass, density, and the viscosity of the fluid it moves through.

FIG. 4—Equation 3 relates a particle's velocity to its mobility and an applied force.

FIG. 5—Equation 4 relates a particle's velocity to its mobility, charge, and applied voltage.

FIG. 6—Equation 5 defines the electrophoretic mobility of a particle from its mobility and charge.

FIG. 7A—Equation 6a defines the Svedberg Coefficient of a particle as its sedimentation velocity divided by the centrifugal acceleration.

FIG. 7B—Equation 6b defines the mobility in terms of the Svedberg Coefficient and the centrifugal acceleration.

FIG. 8A—Equation 7a calculates the mobility of an IgG antibody from Equation 2c.

FIG. 8B—Equation 7b calculates the mobility of an IgG antibody from Equation 6b.

DETAILED DESCRIPTION

Theoretical Treatment of Molecular Movement

Figure 9:
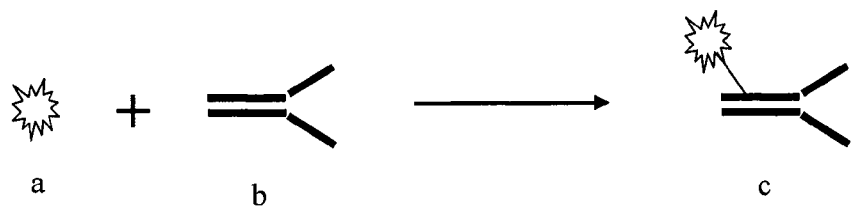
FIG. 9—Fluorescein (a) is conjugated to the First Antibody (b) to form the Signal Generating Antibody (c). Drawings are not to scale, and the individual figures are meant to represent the presence of particular components in a reaction, not the stoichiometric amounts of each component.

A particle (which may be a molecule) moving through a fluid experiences a frictional force proportional to its velocity, its size (as described by its hydrodynamic radius), and the viscosity of the fluid. The formal expression of this as shown in Equation 1 (FIG. 2) is known as the Stokes equation.

The quantity known as the mobility is defined from Equation 1, such that the particle velocity divided by the mobility gives the frictional force. The reason for defining it in this way will become clear shortly. For a spherical molecule, the hydrodynamic radius is equivalent to the radius. For a non-spherical molecule, it is defined as the radius of a spherical molecule that would behave equivalently under creeping flow conditions (which can be theoretically derived if the shape of the molecule is known). The mobility, as extracted from Equation 1, is expressed in Equation 2a (FIG. 3A). If a spherical shape is assumed for a molecule of known molecular weight, then the radius is calculated as shown in Equation 2b (FIG. 3B). Substituting Equation 2b into Equation 2a yields an expression for the mobility in terms of the molecule's density, molecular weight, and viscosity of the fluid, as shown in Equation 2c (FIG. 3C).

The particle moves at a constant velocity when the frictional force due to this movement is equal to an applied force (e.g. gravity, a voltage gradient). Setting the frictional force equal to the applied force and solving for velocity shows that the particle's velocity is simply the applied force multiplied by the mobility, as shown in Equation 3 (FIG. 4). The mobility therefore provides a convenient way for calculating particle velocity. The force experienced by a molecule in an electrical field is proportional to the charge on the molecule and the strength of the field. The velocity of the molecule is therefore given by Equation 4 (FIG. 5), where the quantity designated by "u" is known as the electrophoretic mobility (in units of $cm^2/V\ sec$), defined by Equation 5 (FIG. 6). The factor $10^7$ in Equation 5 converts the charge e into cm-g-s units with volts (which is a m-kg-s unit).

Note that Equation 4 implies that negatively charged molecules (negative ions) move in the opposite direction than positive ions. In the more general form of Equation 4, the velocity of the particle and the electrical field (which is the gradient of the voltage) are vector quantities, and thus have directions associated with them.

The mobility is also closely related to the Svedberg Coefficient s, which is defined as the velocity at which a particle sediments in water at 20° C. in a centrifuge, divided by the centrifugal acceleration. The Svedberg Coefficient is expressed in units of $10^{-13}$ seconds. Using the buoyancy force in Equation 3 to find the velocity, the Svedberg Coefficient as a function of mobility is given by Equation 6a (FIG. 7A). The mobility can therefore be derived from the Svedberg Coefficient as shown in Equation 6b (FIG. 7B).

Immunoglobulin G (IgG or gamma-globulin) is the most common type of antibody found in serum. It has a molecular weight of approximately 150 kDa (1320 amino acid residues). The isoelectric point for different IgG molecules ranges from 6 to 7.5, implying a moderate negative charge to a slight positive charge at neutral pH. The Svedberg Coefficient for IgG is around 7. Assuming a density of about 1.2 $g/cm^3$, the mobility as calculated from Equation 2b is $2.1\times10^7$ s/g, while the mobility as calculated from Equation 6b is $1.7\times10^7$ s/g.

The close correspondence between these two calculations is gratifying, as the first is purely theoretical, while the second has some experimental grounding. The difference between the two come from at least three sources: (1) IgG is not a perfectly spherical molecule, and thus the mobility as determined by sedimentation should be lower; (2) the density of IgG is not known precisely, and this uncertainty is exaggerated in the second calculation and minimized in the first; and (3) the Svedberg Coefficient used in the second calculation is only approximately known. We will take the mobility of IgG to be $2\times10^7$ s/g.

Immunoassays

The importance of measuring protein concentrations in a reliable fashion has led to the development of an abundance of assays involving antibodies or antibody-like molecules. The wide variety of immunoassays currently in use have been described in depth by Gosling (1990), incorporated by reference herein. The descriptions below use antibodies as the binding agents, but in many cases Fab fragments or aptamers could be used instead. However, the methods and compositions described herein are not so limited and in other alternative embodiments, binding agents may be, e.g., biological receptors. A number of such receptors (e.g., insulin receptor, insulin-like growth factor 1 receptor, acetylcholine receptor, GABA receptor, antiotensin receptor, glucagon receptor, chemokine receptors, cytokine receptors, etc.) are well known in the art and any such known receptor or their ligand-binding fragments may be used in the practice of the claimed methods.

Detection and or determination of concentration is typically provided by labeling an antibody or other binding molecule with a signal moiety, such as a fluorescent, chemiluminescent, radioactive or other tag known in the art, allowing the binding molecule to bind to the target, and detecting or measuring the amount of light emission, radioactivity, etc. associated with bound antibody. In most cases, the choice of signaling system is not central to the method. Molecules that are conjugated to antibodies such as FITC or rhodamine for a fluorescent signal can usually be replaced with enzymes such as alkaline phosphatase or horse radish peroxidase if a calorimetric assay is desired, or with enzymes such as carbonic anhydrase or urease for conductivity assays. However, enzymatic assays require the addition of the proper substrate.

A commonly used alternative to conjugating the signaling molecule directly to the antibody that binds the target protein (primary antibody), is to employ a secondary antibody conjugated to the signaling molecule. A secondary antibody is an antibody developed to bind to all antibodies from a certain species (and must therefore be from a different species). For instance, antibodies may be harvested from a goat that has been injected with rabbit antibodies. If these secondary antibodies are conjugated to a signaling molecule, then the binding of the secondary antibody to the primary antibody provides attachment of the signaling molecule to the primary without chemical conjugation. This secondary antibody can be used to attach a signaling molecule to any primary antibody derived from the same species, thereby adding a degree of modularity to the assay.

Heterogeneous immunoassays are often described without specifying the type of solid support to which binding occurs. However, the types of solid supports used represent significant variations in any immunoassay process, affecting both the procedure and the time needed for different steps, and sometimes the type of detection that will be used. For instance, in its most common form, the sandwich ELISA involves binding complexes to the bottom surface of wells in a microtiter plate, which allows for easy manual introduction of reagents for washing, and easy reading of fluorescent or colormetric signals. However, the assay may take several hours due to mass-transfer limitations. It takes time for proteins to equilibrate between the bulk solution and the stagnant layer at the surface, and multiple washes are usually called for. These problems may be mitigated to some extent by using microbeads as the binding surface, which puts the surface into more intimate contact with the bulk solution, as well as drastically increases the surface area available for binding per unit volume of solution. The solid phase (on the beads) is then separated from the solution phase during washing either by filtration or centrifugation. This process may be made more amenable to automation by using paramagnetic beads, which are easily separated from the solution phase magnetically. Nearly all of the heterogeneous immunoassays could be modified to use these different surfaces.

There are two common types of immunoassays in use for detection and/or determination of molecule concentration in samples that are somewhat analogous to the methods described herein. The first, sandwich ELISA, is considered the gold standard for immunoassays in terms of specificity. This high degree of specificity is achieved by requiring the simultaneous binding of two separate antibodies to the target of interest, a technique that is also used in the methods described below. The second is the Affinity Probe Capillary Electrophoresis assay (APCE). This assay consists of binding the target of interest to a single primary antibody, then running the mixture through a capillary electrophoresis device to separate bound antibody from unbound antibody. The electrophoretic separation allows the entire assay to be performed in solution, a technique that is also used in the methods described below.

Sandwich ELISA

The sandwich Enzyme-Linked ImmunoSorbant Assay (ELISA), was first developed in the 1950's as a radio-immunoassay by Rosalyn Yalow and Solomon Berson, and is considered the gold standard for protein detection, exhibiting very high specificity and precision as its primary advantages (Gosling, 1990). Its primary disadvantages are the time it takes and the large number of steps required. The procedure generally takes between two and six hours to perform, depending on the stringency of the washes, and the length of the incubation steps.

The first step is to bind a primary antibody to the target protein to the bottom surface of the wells, that surface having been prepared to promote protein binding. The surface is then treated with a blocker such as bovine serum albumin (BSA), to bind up any remaining active sites, thereby keeping any other proteins from binding and affecting the specificity of the test. The wells are washed multiple times to remove free antibody and blocker.

The sample, presumably containing the target protein, is then added to the well and incubated for a specified time. Ideally, only this target protein will bind to the surface antibody, and no other protein will bind either to the blocked surface or to the surface antibody. Multiple washes are performed to remove any non-specifically bound proteins. If any non-specific proteins do bind, the next step minimizes their effect.

A second antibody to the target protein, conjugated to a detector molecule, is added to the wells and allowed to bind. Because of this antibody's specificity, very little of it will bind to any protein that is non-specifically bound either to the surface or to the first antibody. Ideally, this antibody binds only to target protein bound to the first antibody. Multiple washes are performed to remove any of the unbound second antibody. Because this second antibody is conjugated to a detection molecule, the concentration of this second antibody can be determined and related to the concentration of the target protein in the original sample.

Affinity Probe Capillary Electrophoresis (APCE)

Capillary electrophoresis involves applying a voltage, by means of positively and negatively charged electrodes, across a long capillary filled with an ionic buffer, thereby causing charged molecules to migrate toward one electrode or the other (Oda and Landers, 1997). One common complication is known as "electro-osmotic flow". Glass capillaries tend to have negatively-charged surfaces, which are associated with positively-charged ions in solution near the surface. These positively-charged ions migrate toward the negative electrode (the cathode), dragging the bulk solution with them. This electro-osmotic flow causes all ions to migrate toward the cathode (although at different rates) and is usually put to good use, as a single detector can analyze all ionic species regardless of charge as they flow past. Electro-osmotic flow can be eliminated or even reversed by changing the electrical characteristics of the capillary wall.

For APCE, the target molecule is incubated with a cognate antibody which has been conjugated to a detection molecule, usually a fluorescent probe (Schultz et al., 1997). The mixture is then injected into the capillary, and a voltage is applied, setting up electro-osmotic flow. The free target, the free antibody, and the target/antibody complex will migrate at different rates (augmented by the electro-osmotic flow), and can therefore be detected as separate peaks by a fluorescent detector (the free target should not yield a signal). Although capillary electrophoresis is more rapid than ELISA assays, the small volumes of samples that may be analyzed (due to the small size of the capillary) limits the sensitivity of this method to detect proteins or other target molecules present at very low concentration in the sample.

Enhanced Velocity Electro Immunoassay (EVEIA) for Target Molecule Detection and Quantitation The present application provides a rapid, high sensitivity method for detecting and determining the concentrations of target molecules in samples involving vertical stacked electrophoresis. Because the electrophoretic part of the EVEIA technique takes place in containers of much larger volume and cross-sectional area than microcapillaries, the claimed methods allow the detection of target molecules that are present in low concentration in the sample. In certain preferred embodiments, the electrophoresis may occur in a tube, channel or other container with a minimum hydrodynamic radius (twice the cross-sectional area divided by the circumference) of 0.5 mm or higher.

Figure 10:
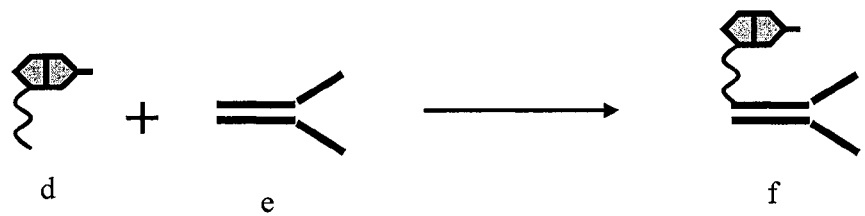
FIG. 10—A biotin derivative (d) is conjugated to the Second Antibody (e) to form the Capture Antibody (f). Drawings are not to scale, and the individual figures are meant to represent the presence of particular components in a reaction, not the stoichiometric amounts of each component.
Figure 11:
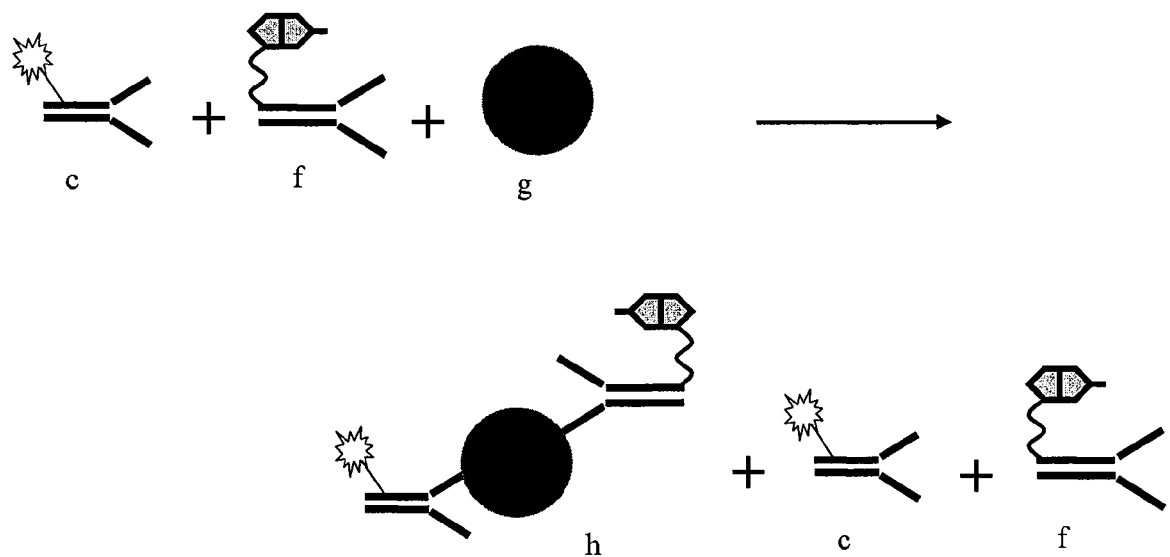
FIG. 11—The Signal Generating Antibody (c), the Capture Antibody (f), and the Target (g) are combined to form the Ternary Complex (h) along with the excess antibodies (c) and (f). Drawings are not to scale, and the individual figures are meant to represent the presence of particular components in a reaction, not the stoichiometric amounts of each component.
Figure 12:
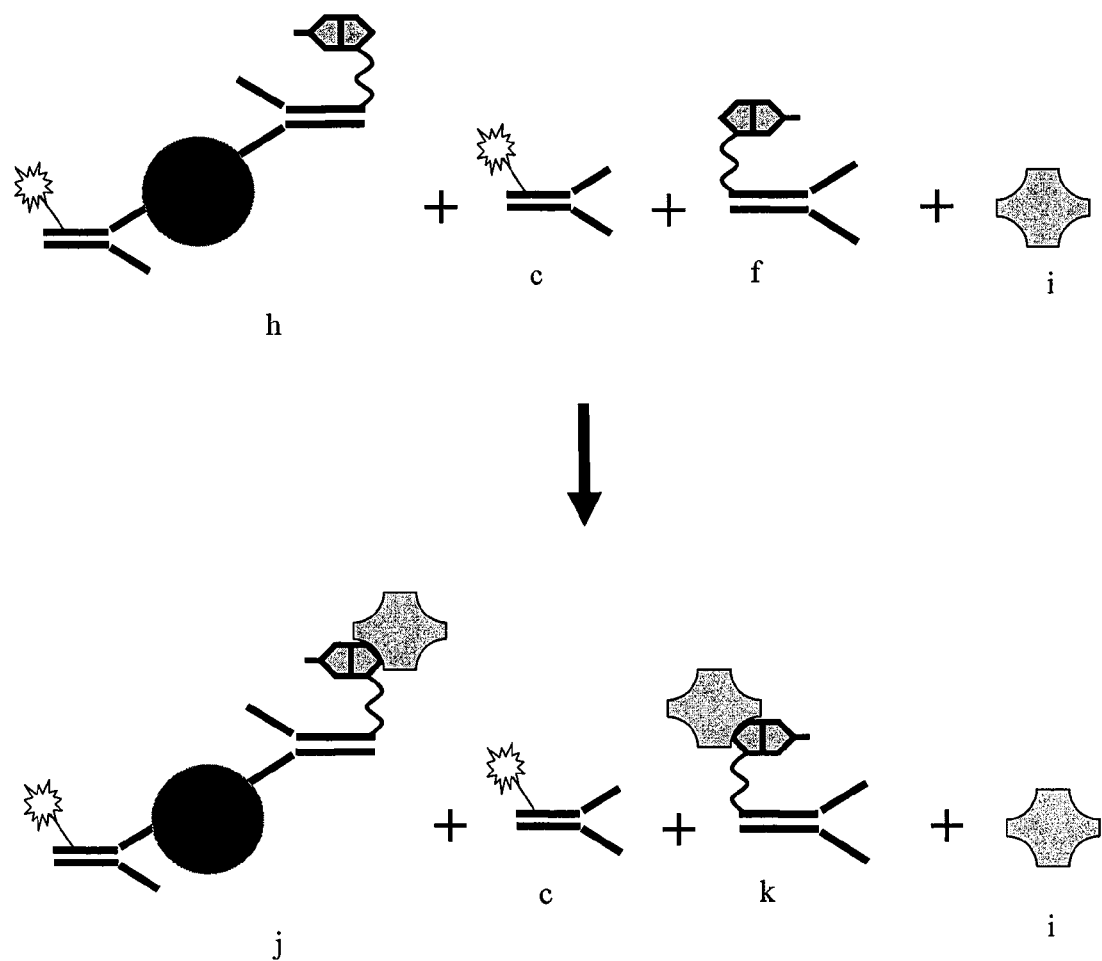
FIG. 12—The resulting mixture from FIG. 11 is mixed with neutravidin (i), which binds with biotin-containing components to form a Neutravidin-Ternary Complex (j), a Neutravidin-Capture Antibody Complex (k), as well as excess Signal Generating Antibody (c) and excess neutravidin (i). Drawings are not to scale, and the individual figures are meant to represent the presence of particular components in a reaction, not the stoichiometric amounts of each component.
Figure 13:
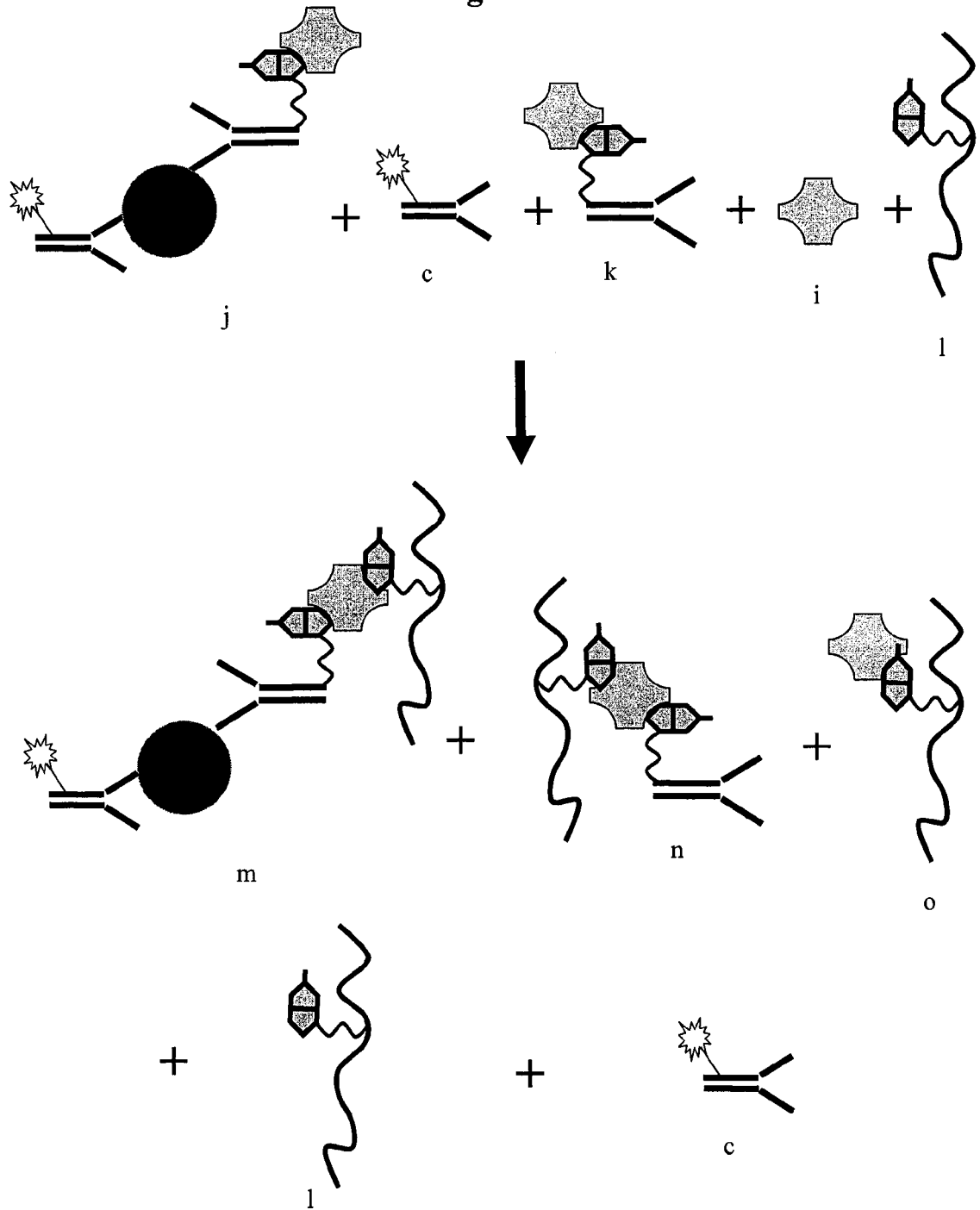
FIG. 13—A voltage applied to the reaction chamber causes the resulting mixture from FIG. 12 to move by electrophoresis into a region containing uncharged polymers conjugated to biotin. Components of the resulting mixture from FIG. 12 that contain neutravidin become bound to the polymers conjugated to biotin. These said polymers are of such size (hundred of thousands to millions of daltons) that the resulting complexes have drastically reduced electrophoretic mobilities compared to any components in the resulting mixture from FIG. 12. Drawings are not to scale, and the individual figures are meant to represent the presence of particular components in a reaction, not the stoichiometric amounts of each component.
Figure 14A:
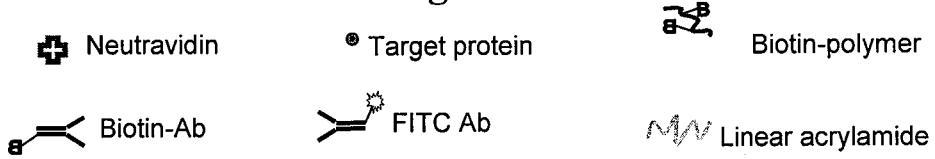
FIG. 14A—Explanation of the individual drawings used to represent the various components in this figure, including neutravidin, target protein, biotin-conjugated polymer, Capture Antibody, Signal-Generating Antibody, and the polymer in the Stacking Layer. Drawings are not to scale, and the individual figures are meant to represent the presence of particular components in a reaction, not the stoichiometric amounts of each component.
Figure 14B:
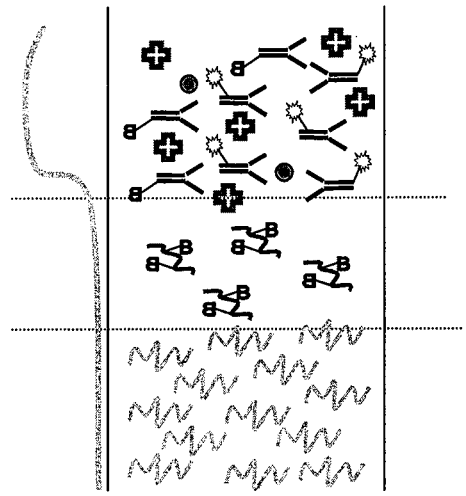
FIG. 14B—The initial state of the Reaction Chamber, which is divided into the three layers from top to bottom: the Sample Layer, the Capture Layer, and the Stacking Layer, respectively. The Sample Layer is composed of the components on the left-hand side of the reaction equation in FIG. 11, plus neutravidin in reaction buffer. The Capture Layer contains the non-charge, biotin-conjugated polymer in reaction buffer. The Stacking Layer contains a non-charged polymer such as linear polyacrylamide. The gray trace shown on the left side of the chamber in each figure represents the detectable amounts of the Signal-Generating Antibody at each point.
Figure 14C:
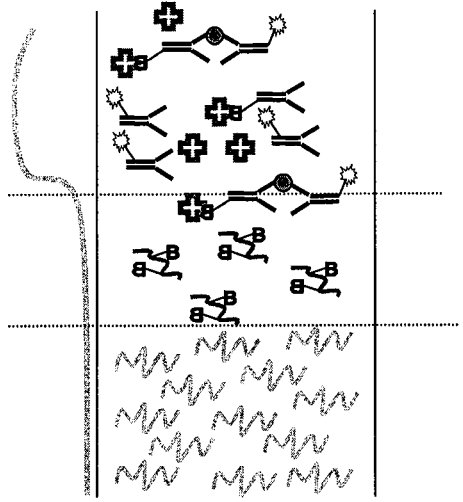
FIG. 14C—Self assembly of complexes in the Sample Layer, represented by the reaction equations in FIG. 11 and FIG. 12.
Figure 14D:
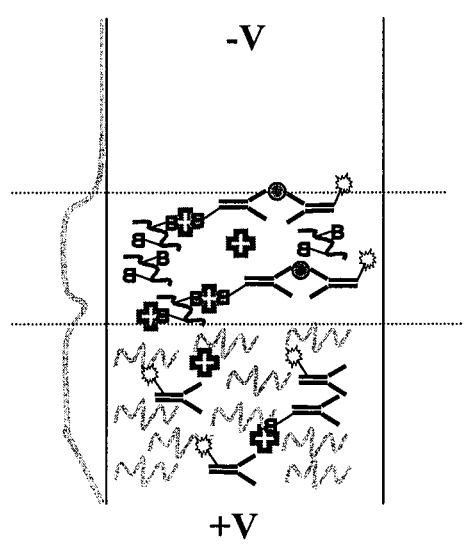
FIG. 14D—Application of a voltage potential in the vertical direction, leading to the electrophoresis of all components into the Capture Layer, leading to the formation of complexes represented by the reaction equation in FIG. 13.
Figure 14E:
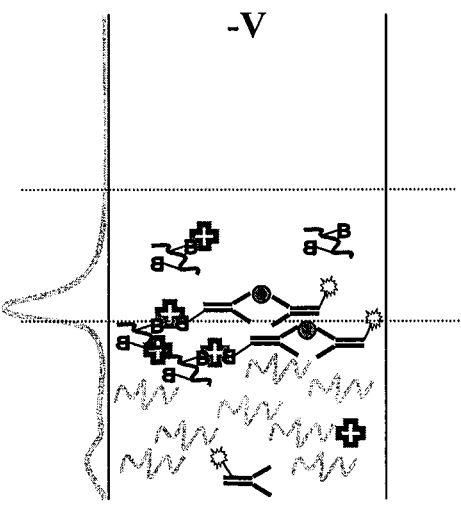
FIG. 14E—Further application of the voltage potential, leading to the movement both into, and through, the Stacking Layer of all complexes not bound to the biotin-conjugated polymer, and the concentration of the bound complexes at the interface between the Capture Layer and the Stacking Layer.

In preferred embodiments, the claimed methods consist of the following steps:

1. Acquiring a first binding agent to the target of interest and conjugating a signaling agent to it in a manner that does not interfere with the specific binding to the target of interest. This said first binding agent could be a monoclonal antibody, an antibody fragment (e.g., Fab), an aptamer, or any other molecule or complex of molecules that exhibit specific binding to the target of interest. The target of interest could be a protein, a protein complex, or any molecule soluble in aqueous solution. The signaling agent could be a fluorescent molecule, a radiolabel, an enzyme that produces a colorimetric product, an enzyme that produces a electrically detectable product, or any molecule or complex of molecules that can be easily detected and quantified, either directly or indirectly. In one preferred embodiment as shown in FIG. 9, the first binding agent is a monoclonal antibody, and the signaling agent is fluorescein.
2. Acquiring a second binding agent to the target of interest and conjugating a capture agent to it in a manner that does not interfere with the specific binding to the target of interest. This second binding agent could be a monoclonal antibody, a polyclonal antibody, an antibody fragment (e.g., Fab), an aptamer, or any other molecule or complex of molecules that exhibit specific binding to the target of interest. The capture agent could be biotin, streptavidin, a single-stranded nucleic acid, or any other molecule or complex of molecules that can be bound with high specificity and affinity. In one preferred embodiment, the second binding agent is a polyclonal antibody, and the capture agent is biotin (as shown in FIG. 10) complexed with neutravidin (as shown in FIG. 12).
3. Acquiring a sample putatively containing some amount of said target of interest, of which amount it is desired to be determined.
4. Preparing a vertical electrophoresis chamber consisting of stacked layers of conductive aqueous solutions, some of which contain uncharged polymers, these layers to be arranged with increasing densities from top to bottom to suppress mixing. The topmost layer will consist of the sample to be measured ("sample layer"). At least one of the layers below the sample layer will contain polymers conjugated to a cognate binding agent of the capture agent ("capture layer"). Optionally, at least one of the layers below the capture layer will contain a relatively high concentration of uncharged polymers, which will serve to impede the mobility of complexes bound to polymers ("stacking layer").
5. Mixing and incubating said first binding agent, said second binding agent, and said target of interest together to allow the formation of ternary complexes, which consist of the first binding agent conjugated to the signaling agent which is bound to the target of interest which is bound to the second binding agent conjugated to the capture agent. This step is shown in FIG. 11, FIG. 12, and FIGS. 14B and 14C for one preferred embodiment of the invention, in which the capture agent is biotin bound to neutravidin.
6. Applying an electrical potential across the vertical dimension of the electrophoresis chamber containing the mixture thereby causing all said molecules to migrate into the capture layer, where it is expected and desired that the ternary complexes will bind to the polymers conjugated to a cognate of the capture agent, thereby drastically reducing the mobility of these said ternary complexes. This step is shown in FIG. 13 and FIG. 14D for one preferred embodiment of the invention.
7. Continuing the application of the electric potential thereby effecting a separation between the low-mobility ternary complexes bound to polymers, and all other molecules, thus localizing in time and space the signaling agents associated with the target of interest from all other signaling agents. This step is shown in FIG. 14D for one preferred embodiment of the invention.
8. Optionally, continuing the application of the electric potential, thereby causing all said molecules to migrate into the stacking layer, in which the mobility of the ternary complexes is further reduced, leading to a compression of the band containing these ternary complexes, and effecting a further separation between the low-mobility ternary complexes that are bound to polymers, and all other molecules. This step is shown in FIG. 14E for one preferred embodiment of the invention.
9. Measuring the signaling agent in one or more of these said groups of compounds, thereby determining the amount of said target of interest in said sample.

EXAMPLES

The following Examples are meant to illustrate preferred embodiments of the invention and are not limiting as to the scope of the claimed subject matter. The skilled artisan will realize that other compositions, apparatus or steps known in the art, or variation in the sequence of the steps, may be utilized.

Example 1

Detection of the Protein Transferrin

1. A rabbit-derived monoclonal antibody which binds specifically to human transferrin is conjugated to fluorescein and the conjugated antibody is purified.
2. A second rabbit-derived monoclonal antibody which binds specifically to human transferrin, without competing with the first antibody for binding to transferrin is conjugated to biotin and the conjugated second antibody is purified.
3. A vertical electrophoresis chamber is prepared, consisting of two stacked layers of conductive aqueous solutions containing essentially uncharged polymers. These layers are arranged with increasing densities from top to bottom to suppress mixing. The top layer consists of biotin-conjugated dextran in reaction buffer ("capture layer"). The bottom layer consists of linear polyacrylamide in reaction buffer ("stacking layer").
4. These two conjugated antibodies and neutravidin are mixed with the sample at a concentration of 1 nM of the antibody conjugated to fluorescein, 10 nM of the antibody conjugated to biotin, and 10 nM of neutravidin. This mixture is incubated at 37° C. for 5 minutes.
5. The sample/antibody mixture is layered on top of the capture layer of the electrophoresis chamber described in step 3, and a potential of 100 V/cm is applied for 5 minutes. One preferred embodiment for such a device is shown in FIG. 14.
6. The reaction chamber is illuminated during step 5 with light at 475 nm, and the fluorescent signal near the interface of the capture and stacking layers is measured with a fluorescent detector such as a CCD camera with a 500 nm high-pass filter. A signal equal to 1% of the total fluorescent signal of the signaling agent is found.

7. Calculation (1%×1 nM) shows that transferrin is present in the sample mixture at a concentration of at least 10 pM.

Additionally, samples containing known quantities of transferrin may be analyzed following the above protocol and the relative fluorescence signals and concentrations plotted on a graph to generate a standard curve. The fluorescence signal generated from a sample containing an unknown quantity of transferrin may then be analyzed and this fluorescence signal compared to the standard curve. The quantity of transferrin in the sample may then be extrapolated from the standard curve.

To calculate the electrophoretic mobility, we must know the charge on the IgG. However, because of the variable regions of the molecule, the charge can range from negative to slightly positive. We will take the charge to be −10. From equation 5, the electrophoretic mobility is thus:

$$u=(1.6^{-19})(-10)(2\times10^7)(1\times10^7)=-3.2\times10^{-4}\ cm^2/s\ V$$

Voltages applied in capillary electrophoresis can be as high as 500 V/cm. The limitation is usually heat generation, which is proportional to the square of the applied voltage. In this case, by applying 100 V/cm, the IgG molecule moves at approximately 2 cm/min in the negative direction (toward the positive electrode).

Example 2

Proof of Concept

Figure 15:
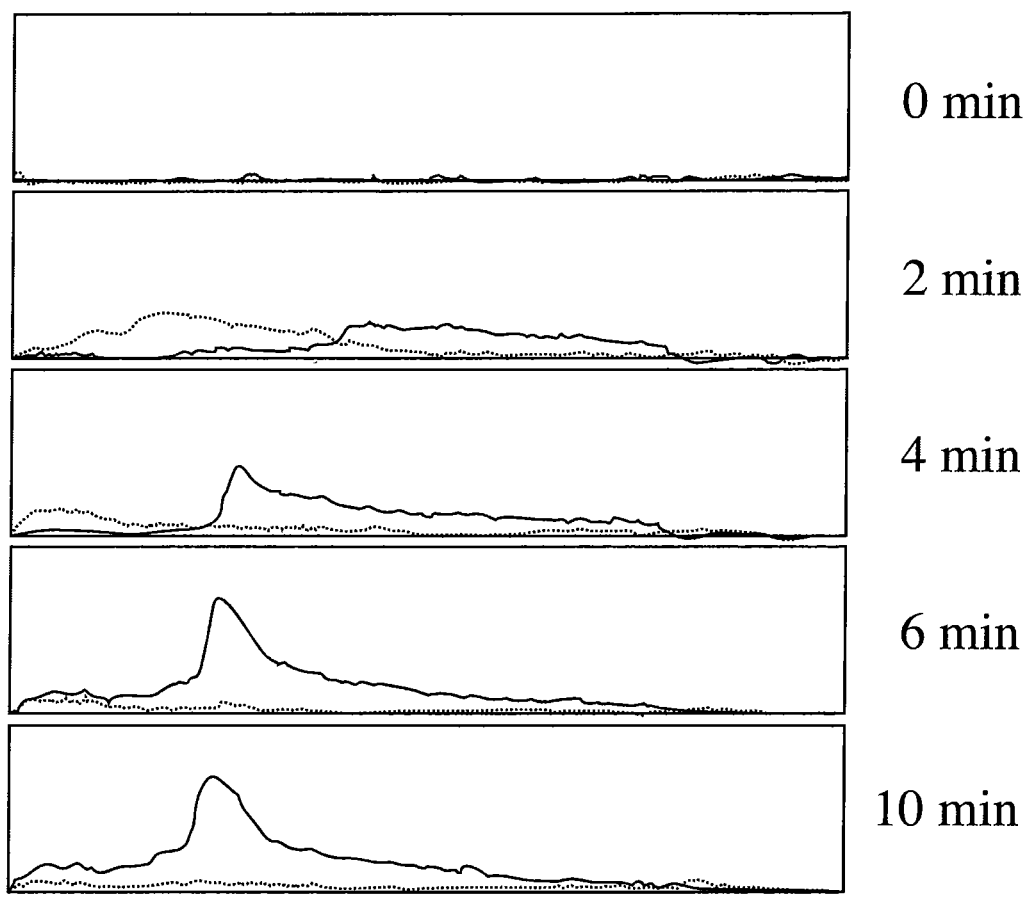
FIG. 15—The dark trace in each plot represents the concentration of FITC-labeled neutravidin in the presence of biotinylated dextran in the Capture Layer, while the light trace represents the concentration of FITC-labeled neutravidin without biotinylated dextran in the Capture Layer.

FIG. 15 shows data from a proof-of-concept experiment. The capture of neutravidin demonstrates how the three-layer design functions to capture desired targets and focuses these targets into bands for detection. The standard electrophoresis cell for this assay was prepared, consisting of three layers: in the bottom ("stacking") layer was linear polyacrylamide in tris-acetate buffer and 7.5% glycerol; in the middle ("capture") layer was biotinylated dextran in tris-acetate buffer and 4% glycerol; and in the top ("sample") layer was FITC-labeled neutravidin in tris-acetate buffer. In the control run, the capture layer had no biotinylated dextran.

The sample layer is located outside of the detection window, to the right in these plots. When a voltage was applied to the cell, the neutravidin migrated (to the left) into the capture layer, where it bound the biotinylated polymer, dramatically slowing its mobility. When the neutravidin-polymer complex reached the stacking layer, the presence of the linear polyacrylamide slowed the progress of the complexed neutravidin nearly to a standstill, focusing the band. Free neutravidin in the control run moved freely through both the capture and the stacking layers.

Example 3

IL-6 Determination

IL-6 was used as an example of the application of the described methods, apparatus and composition to measure biomolecule concentration. As demonstrated, the EVEIA method can generate a signal that increases in a nearly linear fashion across a range of IL-6 concentrations spanning nearly 2.5 concentration logs, representing concentrations of approximately 3 pM to 1000 pM.

Figure 16:
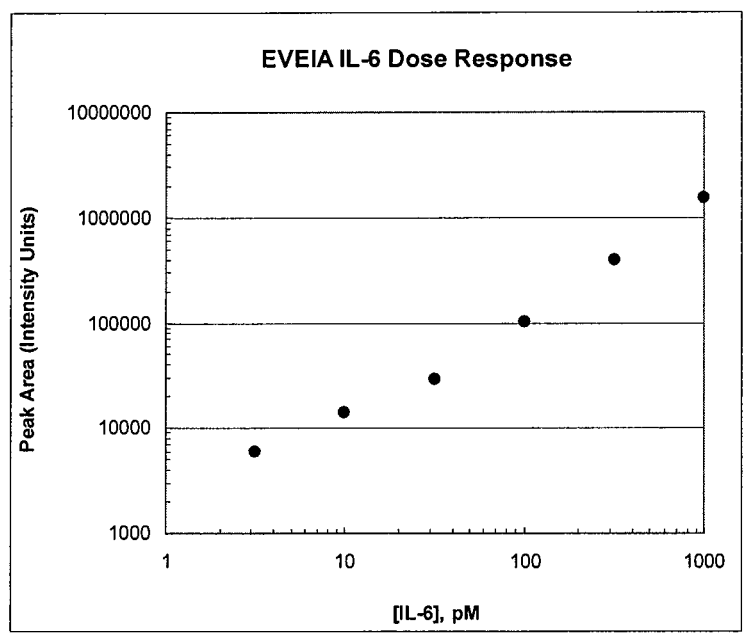
FIG. 16—Dose response data from full sandwich assay for human IL-6.

FIG. 16 shows dose response data from a full sandwich assay for human IL-6. Following the protocol given below generated the data shown in FIG. 16.

Assembling the Apparatus and Buffer System

A 3 mm i.d.×60 mm quartz tube (electrophoresis channel) was assembled between cathode (top) and anode (bottom) buffer reservoirs via gaskets that provided an opening between the buffer reservoirs and the top and bottom of the quartz tube. Bulk fluid flow between the reservoirs and the quartz tube openings was prevented by partitioning the reservoirs and tube ends with gasketed cellulose acetate molecular weight cut-off membranes. Each reservoir was filled with 7.5 ml of 50 mM sodium borate, pH 8.3. The fluid within the electrophoresis channel was set up as a buffered sucrose gradient: the bottom half of the channel (anode end) was filled with running buffer additionally containing 7.5% w/v sucrose and is termed the stacking layer; a 30 µl volume of running buffer additionally containing 5.0% w/v sucrose and 500 nM linear polyacrylamide-conjugated biotin (high molecular weight LPA-B) was layered on top of the stacking layer and is termed the capture layer. Running buffer additionally containing 2.0% sucrose was layered on top of the capture layer, filling the top half of the electrophoresis channel (cathode end). Running buffer was comprised of 150 mM betaine, 0.02% NP-40, 0.01% sodium azide, and 24 mM sodium borate, pH 7.8.

Assay Sample

Figure 17:
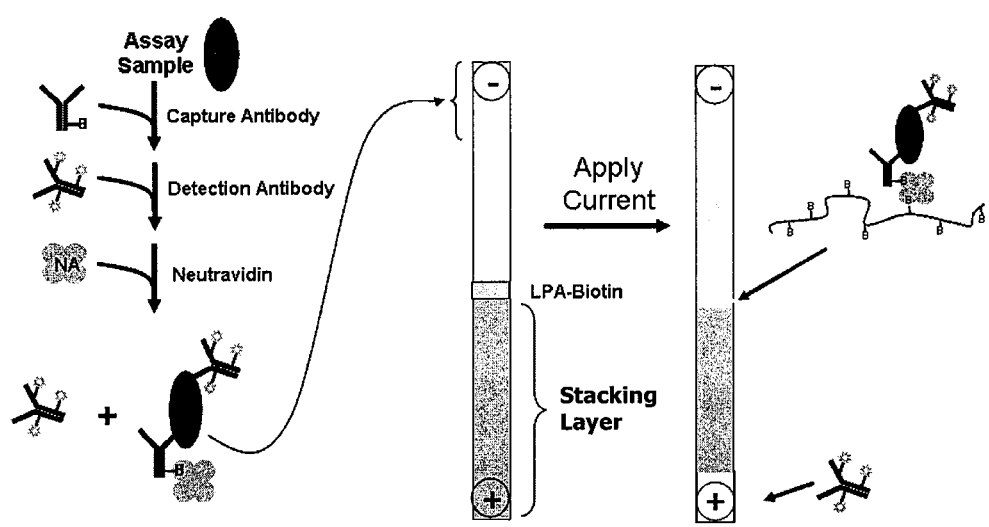
FIG. 17—EVEIA sandwich assay method overview.

The IL-6 dose response assay measured signal was achieved with IL-6 concentrations ranging between 1 pM and 1 nM (half-log dilutions from a 1 nM IL-6 stock) in 50 µl assay sample volumes and included a "no IL-6" control. Each IL-6 dose response binding assay sample was assembled in an Eppendorf® tube. 5 µl of 10 nM fluorescein-labeled anti-IL-6 monoclonal antibody MAB206 (R&D Systems, Minneapolis, Minn.) was added to 5 µl of the appropriate IL-6 dilution. After a 10 min incubation at room temperature, 5 ul of 10 nM biotinylated anti-IL-6 polyclonal antibody BAF206 (R&D Systems) was added. After an additional 10 min incubation at room temperature, 7.5 ul of 500 nM neutravidin (Pierce Biotechnology, Rockford, Ill.) and 27.5 µl of running buffer additionally containing 4.0% w/v sucrose was added to give a 50 µl final assay sample volume. The concentration of each antibody and of neutravidin in each 50 µl assay sample volume were 1 nM and 75 nM, respectively. Sample assembly and the EVEIA method is shown graphically in FIG. 17.

Exemplary Method

The assay sample was prepared by combining the antigen with a biotinylated capture antibody, a fluorescently-labeled detection antibody, and neutravidin. This sample was slowly injected into a vertical electrophoresis channel (e.g., 3 mm i.d.×60 mm quartz tube assembled between a top cathode and bottom anode buffer reservoirs) that was filled with a buffered sucrose density gradient comprised of the following three density layers: top layer comprised of running buffer plus 2% sucrose, a small middle layer (30 µl) comprised of running buffer with 5% sucrose and biotinylated linear polyacrylamide capture polymer (LPA-B), and a bottom layer comprised of running buffer with 7.5% sucrose. Upon the application of voltage (300-900 V) across the channel, the anionic assay sample components migrated towards the bottom of the tube. Sandwich complexes, by virtue of neutravidin binding to the capture antibody, bind to the high molecular weight LPA-B when they reach the middle layer and are essentially immobilized within this middle layer by the very low mobility of the complexes and the sucrose gradient. Unbound assay sample components, including unbound detection antibody electrophoretically migrated to the bottom of the electrophoresis channel. Fluorescence intensity data was recorded in real time and saved throughout the run time. With this example, the excitation light source was a 478 nm laser and detection was with a filtered (appropriate band pass filters for fluorescein-emitted light) CCD camera.

EVEIA Partitioning and Detection

A 40-ul volume of the 50-ul assay sample was slowly injected into the top (cathode end) of the electrophoresis channel with a Hamilton syringe. Electrophoresis was initiated with limits set to 2 mA and 650 V. The channel was irradiated with a 478 nm laser throughout the run. Seven second exposures (CCD camera) were recorded at 30 second intervals over 12 minutes (24 total exposures yielding 24 "fluorescence intensity vs. channel position" plots). The fluorescence intensity data point from each assay sample was taken as the area of the captured sandwich complex peak (i.e., area of the signal peak within the capture layer). A background value, obtained from the "no IL-6" control, was subtracted from the peak area values. A log-log plot of this data is shown in FIG. 16. Dose response was nearly linear over at least 2.5 logs.

Although the Example above described application of the EVEIA technique to IL-6, the skilled artisan will realize that the described methods, compositions and apparatus may be readily applied for the detection and/or determination of concentration of any selected molecule for which antibodies are commercially available or may be readily prepared. Commercial sources of antibody-producing hybridomas against a wide variety of target molecules, of use in the practice of the claimed methods, are well known in the art (e.g., American Type Culture Collection, Manassas, Va.). Techniques for the preparation of monoclonal or polyclonal antibodies, or fragments thereof, against virtually any target of interest are also well known in the art and may be readily employed by the skilled artisan, without requirement for undue experimentation (see, e.g., Harlow and Lane, 1988, incorporated herein by reference in its entirety).

REFERENCES CITED

Drolet D W, Moon-McDermott L, and Romig T S. An Enzyme-Linked Oligonucleotice Assay. Nature Biotechnology, Vol. 14, No. 8, 1996 (pp. 1021-1025).

Gold L, Polisky B, Uhlenbeck O, and Yarus M. Diversity of Oligonucleotide Functions. Annual Review of Biochemistry, vol. 64, 1995 (pp 763-797).

Gosling J P. A Decade of Development in Immunoassay Methodology. Clinical Chemistry, Vol. 36, No. 8, 1990 (pp 1408-1427).

Harlow, E. and Lane, D. Antibodies: A Laboratory Manual. Cold Spring Harbor Laboratory, Cold Spring Harbor, N.Y., 1988.

Oda R P and Landers J P. Introduction to Capillary Electrophoresis, in Handbook of Capillary Electrophoresis. Landers J P, editor. CRC Press, 1997 (pp. 1-48).

Ronkainen-Matsuno N J, Thomas J H, Halsall B, Heineman W R. Electrochemical ImmunoAssay Moving into the Fast Lane. Trends in Analytical Chemistry. Vol 21, No. 4, 2002 (pp. 213-225).

Schultz N M, Tao L, Rose D J, and Kennedy R T. Immunoassays and Enzyme Assays Using Capillary Electrophoresis, in Handbook of Capillary Electrophoresis. Landers J P, editor. CRC Press, 1997 (pp. 611-638).

Shahdeo K and Karnes H T. Combining Immunoassays with Chromatographic and Electrophoretic Separation Techniques—a Review. Mikrochimica Acta, Vol. 129, 1998 (pp. 19-27).

What is claimed is:

1. A method for detecting the presence of a target molecule in a sample performed entirely in solution phase, comprising:
    a) detecting the presence of a target molecule in a sample by subjecting the sample, to determine if the sample contains the target molecule, to electrophoresis entirely in a conductive aqueous solution phase, further comprising
        (i) a first binding agent conjugated to a detection molecule and
        (ii) a second binding agent conjugated to a capture molecule,
    wherein the target molecule, when present in the sample, binds to the first and second binding agents to form a target complex,
    wherein the electrophoresis is performed
        (iii) in stacked layers comprising at least one of each of a sample layer that is mixed with, a capture layer and a stacking layer of entirely conductive aqueous solutions;
    wherein the sample layer comprises the target molecule, detection conjugate and capture conjugate;
    wherein the electrophoresis moves (i) non-complexed and (ii) complexed molecules comprising said target complex through the capture layer, wherein the capture layer comprises uncharged liquid polymers that bind a cognate binding agent provided in the capture molecule;
    wherein the electrophoresis moves said target complex through the capture layer and separates non-complexed molecules from the complexed molecules comprising the target complex that are bound to the uncharged liquid polymers through the cognate binding agent of the capture molecule;
    wherein the electrophoresis moves said complex through the stacking layer, wherein the stacking layer comprises uncharged liquid polymers that impede the mobility of complexes bound to the uncharged liquid polymers that becomes concentrated and immobile in the stacking layer in order to separate the non-complexed molecules from the complexed molecules comprising the target complex that are bound to the uncharged liquid polymers; and
    wherein the presence of the target complex is detected by measuring or detecting the amount or presence of the detection molecule provided in the target complex.

2. The method of claim 1, wherein the binding agents are at least one selected from the group consisting of antibodies or antigen-binding fragments thereof, aptamers, biological receptors or fragments thereof or molecules that specifically bind to the target molecule.

3. The method of claim 2, wherein the antibodies are monoclonal antibodies.

4. The method of claim 1, wherein the target molecule comprises at least one selected from the group consisting of a protein, a protein complex, or a peptide.

5. The method of claim 1, wherein the sample is loaded at the top of a tube, channel or container or the electrophoresis is performed in a gradient of increasing density or viscosity from top to bottom of the tube, channel or container, or the gradient comprises at least two phases of different densities or viscosities, or wherein the tube, channel or container has a hydrodynamic radius equal to twice the cross-sectional area divided by the circumference of at least 0.5 mm.

6. The method of claim 5, wherein the gradient comprises at least two phases of different densities or viscosities.

7. The method of claim 5, wherein the gradient comprises a sample layer mixed with the capture layer and the stacking layer.

8. The method of claim 1, wherein the capture molecule comprises at least one selected from the group consisting of biotin, streptavidin, avidin, neutravidin, and a single-stranded nucleic acid.

9. The method of claim 1, wherein the detection molecule is at least one selected from the group consisting of fluorescent, luminescent, chemiluminescent, a radionuclide or an enzyme that produces a fluorescent, luminescent, chemiluminescent or colored product.

10. An apparatus for detecting a target molecule according to the method of claim 1 comprising:
(a) a vertically arranged tube, channel or container; and
(b) stacked layers comprising at least one of each of a sample layer, a capture layer and a stacking layer, wherein the capture layer and the stacking layer comprise conductive aqueous solutions containing uncharged liquid polymers; and
c) an electrode configured to apply an electrical potential across the vertical dimension of the tube, the channel or the container,
wherein the apparatus further comprises:
a target molecule, a first binding agent conjugated to a detection molecule and a second binding molecule conjugated to a capture molecule, wherein the target molecule, first and second binding molecules are capable of forming a complex in the sample layer; and
a detection device configured for detecting and measuring the detection molecule, wherein the uncharged liquid polymer in the capture layer binds to the capture molecule to become part of the complex;
wherein the sample is configured to vertical stacked electrophoresis using vertical layers of conductive aqueous solutions comprising a sample layer that is mixed with non-gel conductive aqueous solutions as capture and stacking solution layers in the presence of one or more essentially uncharged liquid polymers,
wherein the complex is configured to self-assemble in solution to form a detectable low mobility complex of increase in mass to charge ratio and a decrease in electrophoretic mobility of the target molecule and complex;
wherein the complex is configured to be concentrated at the stacking layer for detection;
wherein the complex is essentially immobile at the stacking layer; and
wherein the portion of the first binding agent that is not part of a complex is configured to migrate through the stacking layer and configured to be separated from the complex to provide said detectable low mobility complex.

* * * * *